United States Patent [19]

Patel et al.

[11] 4,013,064
[45] Mar. 22, 1977

[54] PORT MEANS FOR A LIQUID TRANSPORT SYSTEM

[75] Inventors: Bhupendra C. Patel, Elgin; Frank K. Villari, Oak Park, both of Ill.

[73] Assignee: The Kendall Company, Boston, Mass.

[22] Filed: June 26, 1975

[21] Appl. No.: 590,787

[52] U.S. Cl. .............................. 128/2 F; 128/295; 128/349 R
[51] Int. Cl.² ................. A61B 10/00; A61M 25/00
[58] Field of Search ......... 128/214 R, 214.2, 214.4, 128/275, 295, 2 F, 348–350

[56] References Cited

UNITED STATES PATENTS

| | | | |
|---|---|---|---|
| 2,832,338 | 4/1958 | Ryan | 128/214 R |
| 3,447,570 | 6/1969 | Collins | 128/214 R |
| 3,699,964 | 10/1972 | Ericson | 128/275 |
| 3,734,095 | 5/1973 | Santomieri | 128/214.4 |
| 3,898,988 | 8/1975 | Morgan | 128/214 R |
| 3,900,028 | 8/1975 | McPhee | 128/272 |

*Primary Examiner*—Dalton L. Truluck
*Attorney, Agent, or Firm*—Powell L. Sprunger

[57] ABSTRACT

Port means for a liquid transport system comprising, a relatively rigid body member having an inner surface defining a lumen, and an opening extending through a side of the body member and communicating between the lumen and the outside of the body member. The port means has a flexible closure member having a plug received in the opening of the body member. The plug has an inner surface defining a sidewall of the lumen, and the closure member has an outer surface defining a location for receiving a needle to penetrate the plug and establish communication with the lumen by a tip of the needle. Means is provided for securing the closure member to the body member with the plug received in the opening.

14 Claims, 8 Drawing Figures

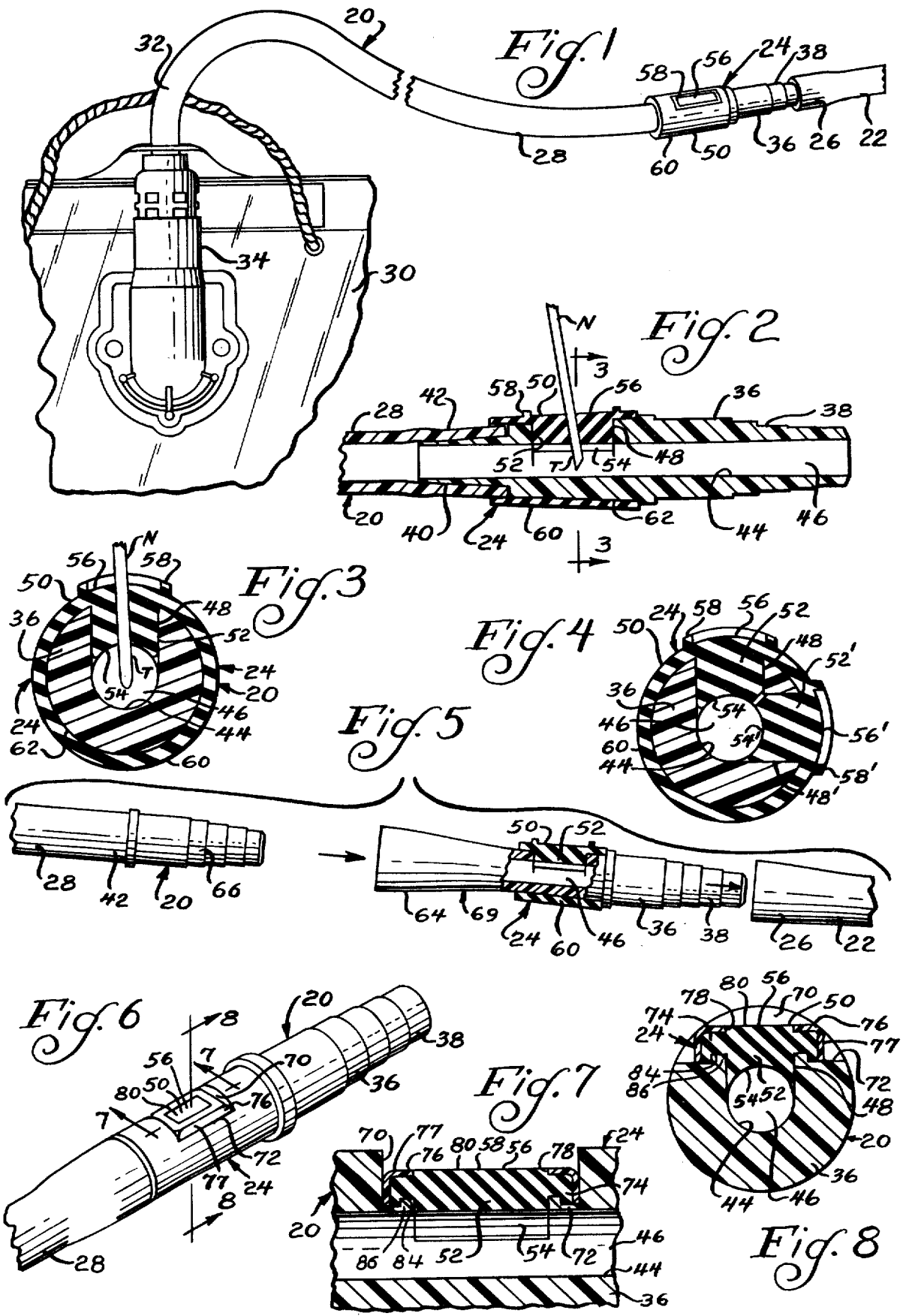

PORT MEANS FOR A LIQUID TRANSPORT SYSTEM

BACKGROUND OF THE INVENTION

The present invention relates to liquid drainage systems, and more particularly to sampling ports for such systems.

Closed drainage systems have been utilized to drain urine from the bladder of a patient in the following manner. A catheter is inserted through the urethra of the patient until a distal end of the catheter containing a drainage eye is located in the bladder, and a retention balloon is inflated through an inflation lumen to retain the catheter in place in the patient. An upstream end of a drainage tube is connected to a proximal end of the catheter which extends outside the patient's body, and a downstream end of the drainage tube communicates with a drainage or collection bag. With the drainage system in place, urine drains from the bladder through the drainage eye, a lumen in the catheter, and a lumen in the drainage tube to the drainage bag where the urine is collected.

Periodically it is desirable to obtain a fresh sample of urine from the closed system for analysis. The sample must be obtained in a manner without affecting the closed nature of the system, since bacteria may otherwise be introduced into the system resulting in possible infection and harm to the patient. In the past, samples have often been obtained by obstructing the proximal end of the catheter, such as by hemostat, after which a needle is punctured through the wall of the catheter, and the urine sample is withdrawn from the catheter lumen through use of a syringe attached to the needle. It has been found that such a procedure is unsatisfactory, since the needle puncture leaves a hole in the sidewall of the catheter. In certain of the catheters, such as a plastic or silicone catheter, the sidewall of the catheter does not seal around the hole thus exposing the catheter lumen to the atmosphere. In other catheters, such as a latex catheter, the hole may be initially sealed, but when the catheter is stretched or bent during subsequent use of the system, the hole may be opened such that the interior of the system is exposed to the atmosphere, which may result in contamination of the closed system. Also the needle may inadvertently puncture the inflation lumen of the catheter, resulting in deflation of the retention balloon.

SUMMARY OF THE INVENTION

A principal feature of the present invention is the provision of port means for a closed drainage system to obtain a sample of liquid from the drainage system without contaminating the system.

The port means of the present invention comprises, a relatively rigid body member having an inner surface defining a lumen, and an opening extending through a side of the body member and communicating between the lumen and the outside of the body member. The port means has a flexible closure member having a plug received in the opening of the body member. The plug has an inner surface defining a sidewall of the lumen, and the closure member has an outer surface defining a location for receiving a needle. Means is provided for securing the closure member to the body member with the plug received in the opening.

A feature of the present invention is that a tip of the needle may be passed through the plug in order to obtain a liquid sample from the lumen.

Another feature of the invention is that the closure member seals the system to prevent contamination of the system after removal of the needle from the closure member.

Yet another feature of the invention is the provision of means for indicating the location for puncturing the outer surface of the closure member to obtain a sample.

Still another feature of the invention is that the inner surface of the plug and the inner surface of the body member define a relatively continuous inner side wall of the lumen to prevent collection of sediment and possible contamination to the system.

A feature of the present invention is the provision of a flexible band in the closure member extending around an outer surface of the body member to retain the plug in place in the opening.

Yet another feature of the invention is that one end of the body member may be secured to an upstream end of a drainage tube.

Another feature of the invention is that an end of the band may cover the upstream end of the drainage tube secured to the body member.

Still another feature of the invention is that the body member may have opposed ends for attachment to a catheter and a drainage tube.

Another feature of the invention is that in one embodiment the securing means may comprise a retaining member which extends peripherally around the closure member.

Further features will become more fully apparent in the following description of the embodiments of this invention and from the appended claims.

DESCRIPTION OF THE DRAWINGS

In the drawings:

FIG. 1 is a fragmentary perspective view of a liquid drainage system showing port means of the present invention in the drainage system;

FIG. 2 is a sectional view of the port means of the present invention;

FIG. 3 is a sectional view taken substantially as indicated along the line 3—3 of FIG. 2;

FIG. 4 is a sectional view of another embodiment of the port means of the present invention;

FIG. 5 is an exploded elevational view of a liquid drainage system, showing the port means in the form of an adapter of the present invention;

FIG. 6 is a perspective view of another embodiment of the port means of the present invention;

FIG. 7 is a fragmentary sectional view taken substantially as indicated along the line 7—7 of FIG. 6; and FIG. 8 is a sectional view taken substantially as indicated along the line 8—8 of FIG. 6.

DESCRIPTION OF THE PREFERRED EMBODIMENTS

Referring now to FIG. 1, there is shown a closed liquid drainage system generally designated 20 having a catheter 22, port means generally designated 24 connected to a proximal end 26 of the catheter 22, a drainage tube 28 extending from the port means 24, and a drainage bag 30 having a chamber communicating with a downstream end 32 of the drainage tube 28 through a drip chamber 34. In use of the drainage system 20, a distal end (not shown) of the catheter 22 is positioned in the patient's bladder with a drainage eye of the catheter located in the bladder. A retention balloon adjacent the distal end of the catheter is inflated through an inflation lumen in a side arm of the catheter to retain the catheter in place in the patient. The urine drains from the bladder through the drainage eye, a lumen in the catheter, the port means 24, a lumen in the drainage tube 28, the drip chamber 34, and into the chamber in the drainage bag 30 for collection therein.

Referring now to FIGS. 1–3, the port means 24 has a relatively rigid connecting or body member 36, which may be made of any suitable material, such as plastic. The connecting or body member 36 has an upstream end 38 which is removably received within the proximal end 26 of the catheter 22, a downstream end 40 received in an upstream end 42 of the drainage tube 28, and an inner surface 44 defining a sidewall of a lumen 46 which extends between the upstream end 38 and the downstream end 40 of the connecting member 36. The connecting member 36 also has an opening 48 extending between the lumen 46 and the outside of the connecting member.

The port means 24 also has a flexible closure member 50 which may be made of any suitable material, such as latex. The closure member 50 has a flexible plug 52 received in and closing the opening 48 of the connecting member 36. In a preferred form, sidewalls of the plug 52 sealingly engage against sidewalls of the opening 48 to prevent pooling of urine and collection of sediment between the plug and the connecting member; the plug also seals the opening to prevent contamination to the system. As shown, the plug 52 has an inner surface 54 which defines a portion of the sidewall of the lumen 46. In a preferred embodiment, the inner surface 44 of the connecting member 36 and the inner surface 54 of the plug 52 define a relatively continuous inner sidewall of the lumen 46 also to prevent collection of sediment and pooling of urine in the lumen which otherwise might result in development of bacteria in the closed drainage system. Thus, if the lumen 46 has a generally cylindrical shape, the inner surface 54 of the plug 52 defines a portion of the cylindrical lumen 46.

The closure member 50 also has an outer surface 56 defining a location for receiving the tip T of a needle N. The closure member 50 may have a rib 58 extending outwardly from the outer surface 56 of the closure member. The rib 58 extends around the location of the underlying plug 52 to indicate a region within the rib 58 at which the closure member may be punctured for passage of the needle tip T through the plug 52 to the lumen 46. The closure member 50 also has a flexible band 60 which extends from the plug around an outer surface 62 of the connecting member 36 to retain the plug 52 in place within the opening 48 of the connecting member 36. In this configuration, the band 60 is slightly stretched to retain the plug 52 properly positioned within the opening 48. Thus, the plug 52 and band 60 automatically seal the opening 48 and lumen 46 of the connecting member 36 from the atmosphere, without the requirement of additional sealing means, such as adhesive. Of course, it will be understood that any other suitable means may be utilized to secure the plug 52 within the opening 48 of the connecting member 36. The closure member 50 may be readily positioned on the connecting member 36 by stretching the band 60 slightly, and by sliding the closure member over the connecting member until the plug is located in the opening 48 of the connecting member 36, after which the closure member is released. In a preferred form as shown, the band 60 extends a sufficient distance downstream to cover a portion of the upstream end 42 of the drainage tube 28 and provide a relatively unbroken surface between the closure member 50 and the drainage tube 28.

When it is desired to obtain a urine sample, the drainage tube 28 is clamped downstream the connecting member 36 until a sufficient amount of urine is collected in the connecting member, the outside of the closure member 50 is prepped, and the sterile tip T of the needle N may be inserted through the closure member between the rib 58 until the tip T is located in the lumen 46 of the connecting member 36. Next, the urine may be withdrawn through the needle by suitable means, such as by a syringe attached to the needle. After the sample has been taken, the needle may be withdrawn from the closure member 50, and the flexible closure member seals the puncture to prevent contamination to the closed drainage system 20. Thus, the sample may be taken in an aseptic manner without contamination of the system, and since the connecting member 36 is relatively rigid, the connecting member 36 prevents flexation of the closure member adjacent the site of puncture, and prevents exposure of the lumen 46 to the atmosphere through the puncture.

Also, since the closure member 50 is spaced from the catheter, the danger of inadvertently puncturing the inflation lumen in the catheter is prevented. If desired, the needle may be inserted through the closure member 50 a reasonable number of times to obtain a plurality of samples without contamination of the system.

Another embodiment of the present invention is illustrated in FIG. 4, in which like reference numerals designate like parts. In this embodiment, the connecting member 36 has a second opening 48' extending between the lumen 46 and the outside of the connecting member 36, with the opening 48' being disposed peripherally around the connecting member 36 and generally at a right angle relative the opening 48. The closure member 50 has a second plug 52' projecting inwardly from the band 60 of the closure member 50, with the plug 52' being received in and closing the second opening 48'. The second plug 52' has an inner surface 54' defining a relatively continuous sidewall with the inner surface 54 of the plug 52 and the inner surface 44 of the connecting member 36. The closure member 50 also has a rib 58' extending outwardly from the band 60 and defining a location of an outer surface 56' of the closure member intermediate the rib 58' for puncturing through the plug 52' to the lumen 46 of the connecting member 36. Thus, in this embodiment, the port means 24 has a pair of plugs 52 and 52' through which samples of urine may be obtained from the lumen 46 through use of the needle. The plugs 52 and 52' are disposed generally at right angles in order that the needle being passed through one plug goes not also puncture the other plug.

Another embodiment of the port means 24 of the present invention is illustrated in FIG. 5, in which like reference numerals designate like parts. In this embodiment, the connecting member 36 may comprise an adapter 69 having a hollow downstream end 64 to removably receive a connector 66 secured to the upstream end 42 of the drainage tube 28. As before, the upstream end 38 of the connecting member 36 or adapter 69 is removably received in the proximal end 26 of the catheter 22. In other respects, the port means 24 may be constructed in a manner similar to that described elsewhere in the specification.

Another embodiment of the present invention is illustrated in FIGS. 6-8, in which like reference numerals designate like parts. In this embodiment, the connecting member 36 has a cutout 70 to receive the closure member 50, the cutout 70 defining a ledge 72 for placement of an outer portion of the closure member 50. As before, the plug 52 is received in an opening 48 in the connecting member 36, with an inner surface 54 of the plug defining a relatively continuous sidewall of the lumen 46 relative an inner surface 44 of the connecting member 36. In this embodiment, the plug 52 has a flange 74 extending peripherally around the plug 52, with the flange 74 engaging against the ledge 72 of the connecting member 36 when the plug 52 is positioned within the opening 48 of the connecting member 36. The flange 74 defines an inner recess 84 extending peripherally around the plug 52, and the recess 84 snugly receives a flange 86 which extends outwardly from the ledge 72 peripherally around the opening 48. The port means 24 also has a retaining member 76 which may be made of any suitable material, such as plastic. The retaining member 76 has an L-shaped flange or rim 77 extending peripherally around the plug 52, with the flange 74 of the closure member being received beneath the rim 77 of the retaining member 76, and with the rim 77 defining an opening 78 at a location above the plug 52. The closure member 50 also has an outer portion 80 extending into the opening 78 of the retaining member 76, and defining relatively continuous outer surface with the outer surface of the retaining member 76. The retaining member 76 may be secured to the outside of the connecting member 36 in a suitable manner, such as by sonic welding, solvent bonding, or radio frequency sealing, to secure the closure member 36 in place with the plug 52 received in the opening 48 of the connecting member 36.

The use of the device described in connection with FIGS. 6-8 to obtain a urine sample is similar to that described above. The tip of the needle is inserted through the upper portion 80 and the plug 52 of the closure member 50 between the rim 77 of the retaining member 76 until the needle tip is located in the lumen 46 of the connecting member 36. After the sample has been taken the needle is withdrawn from the closure member, and the closure member automatically seals to prevent contamination of the closed drainage system. The interengaging recess 84 and flange 86 provides a secondary seal for the device while the needle is being withdrawn from the plug 52.

The foregoing detailed description is given for clearness of understanding only, and no unnecessary limitations should be understood therefrom, as modifications will be obvious to those skilled in the art.

We claim:

1. Port means for a liquid transport system, comprising:
    a relatively rigid body member having an inner surface defining a sidewall of a liquid transport lumen, and an opening extending through a side of the body member and communicating between the lumen and the outside of the body member;
    a flexible closure member having a plug received in the opening of the body member, said plug having an inner surface defining a sidewall of the liquid transport lumen, and said closure member having an outer surface defining a location for receiving a needle to penetrate the plug and establish communication with the liquid transport lumen by a tip of the needle;
    means for securing the closure member to the body member with the plug received in said opening, the securing means comprising a flexible band of the closure member extending around an outer surface of the body member; and
    a liquid drainage tube secured to one end of the body member and having a lumen in communication with the lumen of the body member, with one end of said band covering the end portion of the tube secured to the body member.

2. The port means of claim 1 wherein the inner surface of the plug and the inner surface of body member define a relatively continuous sidewall of the lumen.

3. The port means of claim 1 wherein the body member has a second end for attachment to a conduit means.

4. The port means of claim 1 wherein the body member has opposed ends which are attachable to a pair of conduit means.

5. The port means of claim 1 in which the body member has a plurality of openings spaced peripherally around the body member, said openings extending between the lumen and the outside of the body member, and in which the closure member includes a plurality of flexible plugs received in said openings.

6. The port means of claim 5 wherein the securing means comprises a flexible band of the closure member extending around an outer surface of the body member, and in which said plugs project from an inner surface of said band.

7. The port means of claim 5 in which the body member has a pair of openings, and said closure member has a pair of corresponding plugs, said openings and plugs being disposed at approximately 90° relative each other peripherally around the body member.

8. The port means of claim 1 wherein said opening and plug have a generally rectangular shape.

9. The port means of claim 1 including means for indicating the location of the plug on the outer surface of the closure member.

10. The port means of claim 9 in which the indicating means comprises a rib extending from the outer surface of the closure member at a location approximately along the sides of the underlying plug.

11. The port means of claim 1 in which said plug at least substantially closes said opening.

12. Port means for a liquid transport system, comprising:
    a relatively rigid body member having an inner surface defining a sidewall of a liquid transport lumen, an opening extending through a side of the body member and communicating between the liquid transport lumen and the outside of the body member, and a cutout defining a ledge adjacent said opening;
    a flexible closure member having a plug received in the opening of the body member, said plug having an inner surface defining a sidewall of the liquid transport lumen, and said closure member having a flange extending at least partially peripherally around the plug adjacent an outer portion of the closure member, with said flange being located on said ledge of the body member, and an outer portion having an outer surface defining a location for receiving a needle to penetrate the plug and establish communication with the liquid transport lumen by a tip of the needle; and means for securing the closure member to the body member with the plug received in said opening, the securing means comprising a retaining member extending around and covering at least a portion of said flange, said retaining member having a rim including an inwardly directed outer portion defining an opening to receive the outer portion of the closure member, said rim having a side portion depending from the outer rim portion, with the outer and side portions of the rim defining a recess to receive the closure member flange, and with the rim side portion being secured to the body member to retain the closure member in place with the closure member flange located intermediate the rim and body member ledge in the rim recess and with the closure member outer portion projecting into the rim opening.

13. The port means of claim 12 in which the outer surface of the retaining member and said outer portion of the closure member defining a relatively continuous outer surface.

14. The port means of claim 12 in which said flange defines an inner recess extending peripherally around the plug, and in which said body member includes a flange extending outwardly from the body member peripherally around said opening, with said body member flange being snugly received in said recess.

* * * * *